US009382293B2

(12) United States Patent
Eisenbach-Schwartz et al.

(10) Patent No.: US 9,382,293 B2
(45) Date of Patent: Jul. 5, 2016

(54) MODIFIED KISSPEPTIN PEPTIDES AND USES THEREOF

(71) Applicant: Yeda Research and Development Co. Ltd., Rehovot (IL)

(72) Inventors: Michal Eisenbach-Schwartz, Rehovot (IL); Matityahu Fridkin, Rehovot (IL); Michal Cardon-Yaakov, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 14/384,685

(22) PCT Filed: Mar. 14, 2013

(86) PCT No.: PCT/IL2013/050248
§ 371 (c)(1),
(2) Date: Sep. 11, 2014

(87) PCT Pub. No.: WO2013/136338
PCT Pub. Date: Sep. 19, 2013

(65) Prior Publication Data
US 2015/0051151 A1 Feb. 19, 2015

Related U.S. Application Data

(60) Provisional application No. 61/610,698, filed on Mar. 14, 2012.

(51) Int. Cl.
C07K 7/64 (2006.01)
C07K 7/06 (2006.01)
A61K 38/00 (2006.01)

(52) U.S. Cl.
CPC ... C07K 7/64 (2013.01); C07K 7/06 (2013.01); *A61K 38/00* (2013.01)

(58) Field of Classification Search
None
See application file for complete search history.

(56) References Cited

U.S. PATENT DOCUMENTS

| 6,800,611 | B2 | 10/2004 | Fujii et al. |
| 7,625,869 | B2 | 12/2009 | Kitada et al. |
| 8,183,212 | B2 | 5/2012 | Fujii et al. |
| 8,592,379 | B2 | 11/2013 | Fujii et al. |
| 8,716,228 | B2 | 5/2014 | Eisenbach-Schwartz et al. |
| 8,778,871 | B2 | 7/2014 | Kitada et al. |
| 2003/0092622 | A1* | 5/2003 | Sato ............ A61K 9/0019 424/85.1 |
| 2005/0004000 | A1* | 1/2005 | Shechter ........ C07H 15/234 514/143 |
| 2011/0046068 | A1 | 2/2011 | Millar et al. |
| 2011/0214189 | A1 | 9/2011 | Gaitanaris et al. |

FOREIGN PATENT DOCUMENTS

| WO | WO 2006/001499 | 1/2006 |
| WO | WO 2007/125619 | 11/2007 |
| WO | WO 2009/047513 | 4/2009 |
| WO | WO 2009/139298 | 11/2009 |
| WO | WO 2010/137022 | 12/2010 |

OTHER PUBLICATIONS

Tomita 2008 "Structure-Activity relationship study and NMR analysis of fluorobenzoyl pentapeptide GPR54 agonists" peptide science 90(4):503-511.*
Cardon et al; "Dysregulation of kisspeptin and neurogenesis at adolescence link inborn immune deficits to the late onset of abnormal sensorimotor gating in congenital psychological disorders" Molecular psychiatry 215(4) pp. 415-425. (2010).
Castellanos et al; "Sensorimotor gating in boys with Tourette's syndrome and ADHD: preliminary results" Biological psychiatry 39(1) pp. 33-41.(1996).
Niida et al; "Design and synthesis of downsized metastin (45-54) analogs with maintenance of high GPR54 agonistic activity" Bioorganic & Medicinal Chemistry Letters 16 pp. 134-137. (2006).
Ornitz et al; "Prestimulation-induced startle modulation in attention-deficit hyperactivity disorder and nocturnal enuresis" Psychophysiology 29(4) pp. 437-451. (1992).
Perry et al; "Sensorimotor Gating Deficits in Adults with Autism" Biological psychiatry 61 pp. 482-486. (2007).
Swerdlow et al; "A preliminary assessment of sensorimotor gating in patients with obsessive compulsive disorder" Biological psychiatry 33(4) pp. 298-301. (1993).
Swerdlow et al; "Impaired prepulse inhibition of acoustic and tactile startle response in patients with Huntington's disease" Journal of neurology, neurosurgery, and psychiatry 58(2) pp. 192-200. (1995).
Tomita et al; "SAR and QSAR Studies on the N-Terminally Acylated Pentapeptide Agonists for GPR54" Journal of Medicinal Chemistry 50,pp. 3222-3228. (2007).
Ueki et al; "Prepulse inhibition of acoustic startle response in mild cognitive impairment and mild dementia of Alzheimer type" Psychiatry and Clinical Neurosciences 60 pp. 55-62. (2006).
International Preliminary Report on Patentability Dated Sep. 16, 2014 From the International Bureau of WIPO Re. Application No. PCT/IL2013/050248.

* cited by examiner

*Primary Examiner* — Adam M Weidner

(57) ABSTRACT

The present application provides synthetic modified peptides of five to seven natural or non-natural amino acids as well as pharmaceutical compositions comprising them, for use in the treatment a disease or disorder presenting behavioral abnormalities associated with impairment of sensory gating function, depression or cognitive impairment, particularly schizophrenia and Alzheimer's disease.

16 Claims, 9 Drawing Sheets

SEQUENCE LISTING

```
<160> NUMBER OF SEQ ID NOS: 14

<210> SEQ ID NO 1
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: para-aminophenylalanine (Pap),
      NH2C6H4(CH2)1-3CO, Fmoc-Pap, FMS-Pap and C5-C20 acyl-Pap
<220> FEATURE:
<221> NAME/KEY: MISC_FEATURE
<222> LOCATION: (2)..(2)
<223> OTHER INFORMATION: Phe, Ile, Leu, Val or Nle
<220> FEATURE:
<221> NAME/KEY: MISC_FEATURE
<222> LOCATION: (4)..(4)
<223> OTHER INFORMATION: Phe, Ile, Leu, Val or Nle
<220> FEATURE:
<221> NAME/KEY: MISC_FEATURE
<222> LOCATION: (5)..(5)
<223> OTHER INFORMATION: Arg, Lys, homo-Arg, homo-Lys or Orn
<220> FEATURE:
<221> NAME/KEY: MISC_FEATURE
<222> LOCATION: (6)..(6)
```

```
<223> OTHER INFORMATION: Trp, beta-(3-benzothienyl)-L-Ala, 6-methyl Trp,
      5-methoxy-Trp, 5-hydroxy-Trp and 5-fluoro-Trp
<220> FEATURE:
<221> NAME/KEY: MISC_FEATURE
<222> LOCATION: (7)..(7)
<223> OTHER INFORMATION: Tyr, His, O-methyl-Tyr and
      2-hydroxy-3-methyl-Phe
<220> FEATURE:
<221> NAME/KEY: MISC_FEATURE
<222> LOCATION: (7)..(7)
<223> OTHER INFORMATION: amidation

<400> SEQUENCE: 1

Xaa Xaa Gly Xaa Xaa Xaa Xaa
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(7)
<223> OTHER INFORMATION: cyclic peptide
<220> FEATURE:
<221> NAME/KEY: MISC_FEATURE
<222> LOCATION: (1)..(1)
<223> OTHER INFORMATION: para-aminophenylalanine (Pap),
      NH2C6H4(CH2)1-3CO, Fmoc-Pap, FMS-Pap and C5-C20 acyl-Pap
<220> FEATURE:
<221> NAME/KEY: MISC_FEATURE
<222> LOCATION: (2)..(2)
<223> OTHER INFORMATION: Phe, Ile, Leu, Val or Nle
<220> FEATURE:
<221> NAME/KEY: MISC_FEATURE
<222> LOCATION: (4)..(4)
<223> OTHER INFORMATION: Phe, Ile, Leu, Val or Nle
<220> FEATURE:
<221> NAME/KEY: MISC_FEATURE
<222> LOCATION: (5)..(5)
<223> OTHER INFORMATION: Arg, Lys, homo-Arg, homo-Lys or Orn
<220> FEATURE:
<221> NAME/KEY: MISC_FEATURE
<222> LOCATION: (6)..(6)
<223> OTHER INFORMATION: Trp, beta-(3-benzothienyl)-L-Ala, 6-methyl Trp,
      5-methoxy-Trp, 5-hydroxy-Trp and 5-fluoro-Trp
<220> FEATURE:
<221> NAME/KEY: MISC_FEATURE
<222> LOCATION: (7)..(7)
<223> OTHER INFORMATION: Tyr, His, O-methyl-Tyr and
      2-hydroxy-3-methyl-Phe
<220> FEATURE:
<221> NAME/KEY: MISC_FEATURE
<222> LOCATION: (7)..(7)
<223> OTHER INFORMATION: amidation

<400> SEQUENCE: 2

Xaa Xaa Gly Xaa Xaa Xaa Xaa
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: 9-fluorenylmethoxycarbonyl (Fmoc) or
      2-sulfo-Fmoc (FMS)
<220> FEATURE:
<221> NAME/KEY: MISC_FEATURE
```

```
<222> LOCATION: (2)..(2)
<223> OTHER INFORMATION: Phe, Ile, Leu, Val or Nle
<220> FEATURE:
<221> NAME/KEY: MISC_FEATURE
<222> LOCATION: (4)..(4)
<223> OTHER INFORMATION: Phe, Ile, Leu, Val or Nle
<220> FEATURE:
<221> NAME/KEY: MISC_FEATURE
<222> LOCATION: (5)..(5)
<223> OTHER INFORMATION: Arg, Lys, homo-Arg, homo-Lys or Orn
<220> FEATURE:
<221> NAME/KEY: MISC_FEATURE
<222> LOCATION: (6)..(6)
<223> OTHER INFORMATION: Trp, beta-(3-benzothienyl)-L-Ala, 6-methyl Trp,
      5-methoxy-Trp, 5-hydroxy-Trp and 5-fluoro-Trp
<220> FEATURE:
<221> NAME/KEY: MISC_FEATURE
<222> LOCATION: (6)..(6)
<223> OTHER INFORMATION: amidation

<400> SEQUENCE: 3

Xaa Xaa Gly Xaa Xaa Xaa
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(7)
<223> OTHER INFORMATION: cyclic peptide
<220> FEATURE:
<221> NAME/KEY: MISC_FEATURE
<222> LOCATION: (1)..(1)
<223> OTHER INFORMATION: para-amino Phe
<220> FEATURE:
<221> NAME/KEY: MISC_FEATURE
<222> LOCATION: (7)..(7)
<223> OTHER INFORMATION: Tyr or His
<220> FEATURE:
<221> NAME/KEY: MISC_FEATURE
<222> LOCATION: (7)..(7)
<223> OTHER INFORMATION: amidation

<400> SEQUENCE: 4

Xaa Phe Gly Leu Arg Trp Xaa
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Fmoc-Phe or FMS-Phe
<220> FEATURE:
<221> NAME/KEY: MISC_FEATURE
<222> LOCATION: (5)..(5)
<223> OTHER INFORMATION: amidation

<400> SEQUENCE: 5

Xaa Gly Leu Arg Trp
1               5

<210> SEQ ID NO 6
<211> LENGTH: 7
<212> TYPE: PRT
```

```
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: para-amino Phe
<220> FEATURE:
<221> NAME/KEY: MISC_FEATURE
<222> LOCATION: (1)..(7)
<223> OTHER INFORMATION: cyclic peptide
<220> FEATURE:
<221> NAME/KEY: MISC_FEATURE
<222> LOCATION: (7)..(7)
<223> OTHER INFORMATION: amidation

<400> SEQUENCE: 6

Xaa Phe Gly Leu Arg Trp Tyr
1               5

<210> SEQ ID NO 7
<211> LENGTH: 7
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: para-amino Phe
<220> FEATURE:
<221> NAME/KEY: MISC_FEATURE
<222> LOCATION: (7)..(7)
<223> OTHER INFORMATION: amidation

<400> SEQUENCE: 7

Xaa Phe Gly Leu Arg Trp Tyr
1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Fmoc- Phe
<220> FEATURE:
<221> NAME/KEY: MISC_FEATURE
<222> LOCATION: (5)..(5)
<223> OTHER INFORMATION: amidation

<400> SEQUENCE: 8

Xaa Gly Leu Arg Trp
1               5

<210> SEQ ID NO 9
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (12)..(12)
<223> OTHER INFORMATION: amidation

<400> SEQUENCE: 9

Cys Tyr Asn Trp Asn Ser Phe Gly Leu Arg Phe Cys
1               5                   10
```

```
<210> SEQ ID NO 10
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(12)
<223> OTHER INFORMATION: cyclic peptide
<220> FEATURE:
<221> NAME/KEY: MISC_FEATURE
<222> LOCATION: (12)..(12)
<223> OTHER INFORMATION: amidation

<400> SEQUENCE: 10

Cys Tyr Asn Trp Asn Ser Phe Gly Leu Arg Phe Cys
1               5                   10

<210> SEQ ID NO 11
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: amidation

<400> SEQUENCE: 11

Cys Phe Gly Leu Arg Trp Cys
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(7)
<223> OTHER INFORMATION: cyclic peptide
<220> FEATURE:
<221> NAME/KEY: MISC_FEATURE
<222> LOCATION: (7)..(7)
<223> OTHER INFORMATION: amidation

<400> SEQUENCE: 12

Cys Phe Gly Leu Arg Trp Cys
1               5

<210> SEQ ID NO 13
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Fmoc-Tyr
<220> FEATURE:
<221> NAME/KEY: MISC_FEATURE
<222> LOCATION: (10)..(10)
<223> OTHER INFORMATION: amidation
```

```
<400> SEQUENCE: 13

Xaa Asn Trp Asn Ser Phe Gly Leu Arg Phe
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (10)..(10)
<223> OTHER INFORMATION: amidation

<400> SEQUENCE: 14

Tyr Asn Trp Asn Ser Phe Gly Leu Arg Phe
1               5                   10
```

MODIFIED KISSPEPTIN PEPTIDES AND USES THEREOF

FIELD OF THE INVENTION

The present invention relates to synthetic peptides and pharmaceutically acceptable salts thereof and pharmaceutical compositions comprising them, and their uses for treating diseases or disorders presenting behavioral abnormalities such as Alzheimer's disease, or in particular diseases or disorders associated with impairment of sensory gating function such as schizophrenia, and/or for treating depression, and/or for improving cognitive function.

BACKGROUND OF THE INVENTION

Schizophrenia is a severe mental disorder that affects about 1% of the population. The etiology of schizophrenia is complex and involves genetic and environmental factors. Schizophrenia is often described in terms of positive, negative and cognitive symptoms. Positive symptoms, such as delusions and hallucinations, are not normally experienced by most individuals. Negative symptoms are deficits of normal emotional responses or of thought processes and cognitive symptoms are cognitive malfunctions. Negative and cognitive symptoms respond less well to medication than positive symptoms, and are contributing more to poor quality of life, functional disability, and the burden on others than do positive symptoms.

Antipsychotics remain the current standard of care for mental disorders including schizophrenia and bipolar mania. The first generation of antipsychotics (typical) such as haloperidol, inhibit dopamine $D_2$ receptors and are moderately effective in treating positive symptoms of schizophrenia, but may cause extrapyramidal movement disorders. Second-generation (atypical) antipsychotics inhibit $D_2$ receptors in conjunction with other receptors (notably 5-hydroxytryptamine 2A ($5-HT_{2A}$) receptors). Atypical antipsychotics have proved less likely to cause movement disorders, but are associated with weight gain, prolactin and glucose elevation, and sedation. Recent data indicate that agents that target metabolic glutamate receptors (mGluRs) could represent a promising new class of antipsychotics, and such agents are now being developed by several companies. Nevertheless, a large trial known as CATIE, sponsored by the US National Institutes of Health, found that 74% of patients discontinue use within 18 months of therapy due to either poor tolerability or incomplete efficacy, indicating a need for novel therapies.

Kisspeptins (formerly known as Metastins), the products of the Kiss1 gene, bind to a G protein-coupled receptor known as GPR54. Kiss1 was originally identified as a human metastasis suppressor gene. The kisspeptin-GPR54 signaling cascade was recognized several years ago as having a fundamental role in the regulation of sex hormones, and is considered to be the gatekeeper of puberty. Moreover, recent studies indicated that kisspeptin serves additional physiological functions in the cardiovascular system, angiogenesis, and in energy balance. In the hippocampus, kisspeptin enhances excitability of granule cells of the dentate gyrus and secretion of the growth factor brain-derived neurotrophic factor (BDNF, Arai and Orwig, 2008). BDNF has important functions in the development of the nervous system and in brain plasticity-related processes such as memory, learning, and drug addiction. Various studies have shown possible links between BDNF and conditions such as depression, schizophrenia, obsessive-compulsive disorder, Alzheimer's disease, Huntington's disease, Rett syndrome, and dementia, as well as anorexia nervosa and bulimia nervosa.

WO 2010/137022 of the same applicant discloses an elevation in mRNA expression of Kiss1 during adolescence (8 weeks) in the hippocampus of naïve mice. Moreover, the regulation of Kiss1 expression in the hippocampus, unlike its expression in the hypothalamus, is immune-dependent. Thus, functional relationships between the presence of immune deficiency (SCID mice), abnormal expression of kisspeptin in the hippocampus at puberty, and impaired processing of information was found (as measured by prepulse inhibition (PPI)) in these mice (Cardon et al., 2010). PPI is the phenomenon by which a low-intensity prepulse stimulus attenuates the response to a subsequent startle-eliciting noise. Deviations in PPI are commonly associated with the pathophysiology of schizophrenia (Braff and Geyer, 1990) yet abnormal PPI was also found in other psychological disorders (Castellanos et al., 1996; Ornitz et al., 1992; Perry et al., 2007; Swerdlow et al., 1993; Swerdlow et al., 1995).

WO 2010/137022 also discloses that administration of the kisspeptin derived peptide Kp-10 (YNWNSFGLRF-$NH_2$) to SCID mice that have impaired PPI response and to several schizophrenia mouse models, improved PPI response levels. It is additionally disclosed that Kp-10 has a potential anti-depressive activity by a tail suspension test and that Kp-10 improves spatial learning and memory in a water maze in several mouse models, indicating its contribution to broad aspects of cognitive functions such as learning and memory.

SUMMARY OF THE INVENTION

In accordance with the present invention, novel modified Kp-10 derived peptides were synthesized and found to improve PPI response in naïve mice and in schizophrenia and Alzheimer's mouse models.

The present invention thus provides a synthetic peptide selected from:

(i) a cyclic or linear peptide of the sequence:

```
                                    (SEQ ID NOs: 2 and 1)
        R1-Xaa1-Gly-Xaa2-Xaa3-Xaa4-Xaa5-NHR2
``` wherein:

$Xaa_1$ is selected from Phe, Ile, Leu, Val, Nle and analogs thereof;

$Xaa_2$ is selected from Leu, Ile, Val, Nle, Phe and analogs thereof;

$Xaa_3$ is selected from Arg, Lys, homo-Arg, homo-Lys, Orn and analogs of Arg;

$Xaa_4$ is selected from Trp and analogs thereof;

$Xaa_5$ is selected from Tyr, His, O-methyl-Tyr and 2-hydroxy-3-methyl-Phe;

$R_1$ is selected from para-aminophenylalanine (Pap), $NH_2C_6H_4(CH_2)_{1-3}CO$, Fmoc-Pap, FMS-Pap and $C_5$-$C_{20}$ acyl-Pap, wherein said $C_5$-$C_{20}$ acyl is derived from a saturated or unsaturated $C_5$-$C_{20}$ fatty acid linked to the α-amino group of Pap; and $R_2$ is H or $(CH_2)_{0-4}CH_3$, and (ii) a linear peptide of the sequence:

```
                                    (SEQ ID NO: 3)
        R1-Xaa1-Gly-Xaa2-Xaa3-Xaa4-NHR2
``` wherein:
Xaa$_1$ to Xaa$_4$ are as defined above;
R$_1$ is 9-fluorenylmethoxycarbonyl (Fmoc) or 2-sulfo-Fmoc (FMS); and
R$_2$ is as defined above,
and pharmaceutically acceptable salts thereof.

The present invention further provides a cyclic synthetic peptide having the sequence:

(SEQ ID NO: 6)

Pap-Phe-Gly-Leu-Arg-Trp-Tyr-NH$_2$.

The present invention further provides a linear synthetic peptide having the sequence: Fmoc-Phe-Gly-Leu-Arg-Trp-NH$_2$ (SEQ ID NO: 8).

The present invention also provides a pharmaceutical composition comprising the synthetic peptides of the invention or a pharmaceutically acceptable salt thereof and a pharmaceutically acceptable carrier.

The synthetic peptides of the invention are also provided for use in the treatment of a disease or disorder presenting behavioral abnormalities associated with impairment of sensory gating function. The disease or disorder can be schizophrenia.

The synthetic peptides of the invention are additionally provided for use in the treatment of depression or of a cognitive impairment.

The synthetic peptides of the invention are also provided for use in the treatment of Alzheimer's disease (AD).

The present invention also provides a method for the treatment of a disease or disorder presenting behavioral abnormalities associated with impairment of sensory gating function, depression or cognitive impairment, comprising administering to a patient in need thereof an effective amount of a peptide of the invention or a pharmaceutically acceptable salt thereof.

DETAILED DESCRIPTION OF THE INVENTION

Figure 1A:
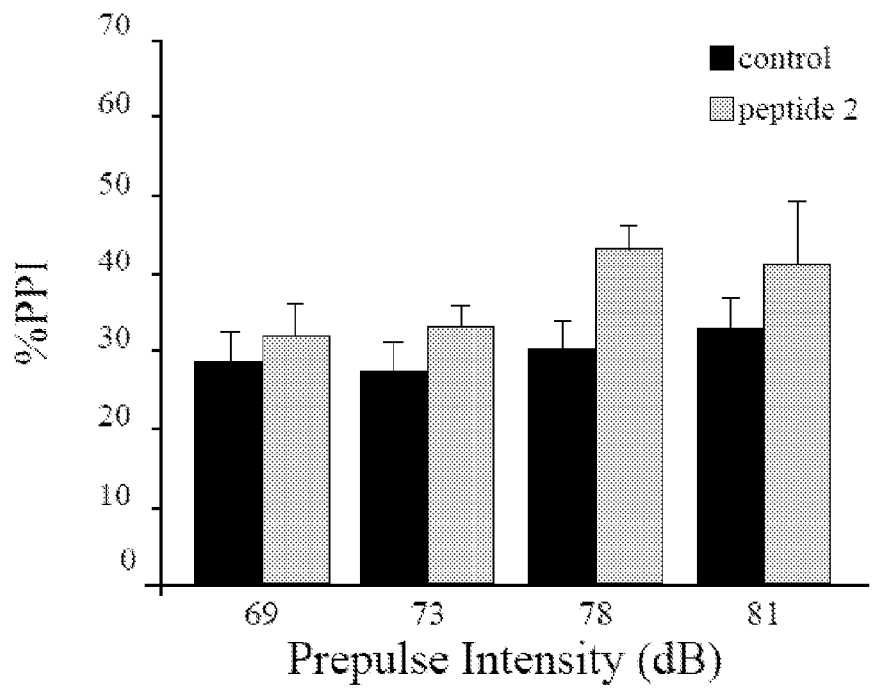
FIGS. 1A-1E show the effect of synthetic peptides on prepulse inhibition (PPI). Male C57B1/6J naïve mice were injected with synthetic peptides (light bars) or with 1% DMSO (control, black bars) in PBS; prepulse intensity was 69, 73, 78 or 81 decibels (dB). (A) 15 μg cyclic Peptide 2 (SEQ ID NO: 10), n=12, control n=8, Repeated measure ANOVA, F (degrees of freedom) (1,18)=4.2, P=0.06. (B) 8.3 μg cyclic Peptide 5 (SEQ ID NO: 12), n=8, control n=6; Repeated measure ANOVA, F (1, 12)=0.1, P=0.7. (C) 8.75 μg cyclic Peptide 6 (SEQ ID NO: 6), n=8, control n=10; Repeated measure ANOVA, F (1, 19)=4.7, P=0.047, * indicates P<0.05, Fisher LSD post hoc analysis. (D) 15.3 μg Peptide 7 (SEQ ID NO: 13), n=12, control n=9, Repeated measure ANOVA, F (1, 18)=1.15, P=0.3. (E) 8.75 μg Peptide 8 (SEQ ID NO: 8), n=17, control n=16, Repeated measure ANOVA, F (1, 31)=5.3, P=0.028, * indicates P<0.05, Fisher LSD post hoc analysis).

The present invention relates to synthetic linear and cyclic peptides which are modified kisspeptin peptide Kp-10 derivatives, and pharmaceutically acceptable salts thereof.

In an attempt to develop Kisspeptin analogs with potentially improved pharmaceutical properties, the inventors designed and prepared several derivatives of Kp-10 (metastin amino acids 45-54), and of Kp-5 (metastin amino acids 50-54), which are described in detail below. The Kp-5 sequence (the last 5 amino acids at the C-terminus of Kisspeptin) forms the binding sequence to GPR54, while the N-terminus of the Kisspeptin is not required for receptor binding, but may be required for stabilization and protection from proteolytic digestion.

In certain embodiments, the synthetic peptides of the present invention are amidated linear peptides represented by the sequence $R_1$-$Xaa_1$-Gly-$Xaa_2$-$Xaa_3$-$Xaa_4$-$Xaa_5$-$NHR_2$. $Xaa_1$ and $Xaa_2$ are hydrophobic amino acids selected from phenylalanine (Phe), isoleucine (Ile), leucine (Leu), valine (Val), norleucine (Nle) and analogs thereof; $Xaa_3$ is a basic amino acid selected from arginine (Arg), lysine (Lys), homo-arginine (homo-Arg), homo-lysine (homo-Lys), ornithine (Orn) and analogs of Arg; $Xaa_4$ is an aromatic amino acid selected from tryptophan (Trp) and analogs thereof; $Xaa_5$ is an aromatic amino acid selected from tyrosine (Tyr), histidine (H is), O-methyl-tyrosine and 2-hydroxy-3-methyl-phenylalanine; $R_1$ is selected from para-aminophenylalanine (Pap), a Pap analog of the formula $NH_2C_6H_4(CH_2)_{1-3}CO$ and Pap attached through the alpha-amino group thereof to a group selected from Fmoc, FMS and $C_5$-$C_{20}$ acyl, wherein said $C_5$-$C_{20}$ acyl is derived from a saturated or unsaturated $C_5$-$C_{20}$ fatty acid; and $R_2$ is a hydrogen atom or an alkyl group having between 1 and 5 carbons (SEQ ID NO: 1).

In certain embodiments, the linear peptides of SEQ ID NO: 1 are cyclized via an azo bond formed between the Pap or Pap analog and the tyrosine or histidine residues to obtain the corresponding cyclic peptides (SEQ ID NO: 2). In general, this cyclization method involves forming an azo bond connecting the side chains of Pap residues to those of tyrosine or histidine residues present in the linear precursors, by using an initial diazotization step in acidic media followed by intramolecular azo cyclization in a mild basic medium.

In certain embodiments, the synthetic peptides of the present invention are amidated linear peptides represented by the sequence $R_1$-$Xaa_1$-Gly-$Xaa_2$-$Xaa_3$-$Xaa_4$-$NHR_2$. $Xaa_1$ and $Xaa_2$ are hydrophobic amino acids selected from phenylalanine (Phe), isoleucine (Ile), leucine (Leu), valine (Val), norleucine (Nle) and analogs thereof; $Xaa_3$ is a basic amino acid selected from arginine (Arg), lysine (Lys), homo-arginine (homo-Arg), homo-lysine (homo-Lys), ornithine (Orn) and analogs of Arg; $Xaa_4$ is an aromatic amino acid selected from tryptophan (Trp) and analogs thereof; $R_1$ is 9-fluorenyl-methoxycarbonyl (Fmoc) or 2-sulfo-Fmoc (FMS); and $R_2$ is a hydrogen atom or an alkyl group having between 1 and 5 carbons (SEQ ID NO: 3).

According to certain embodiments, the synthetic peptides are amidated linear peptides represented by the sequence $R_1$-$Xaa_1$-Gly-$Xaa_2$-$Xaa_3$-$Xaa_4$-$Xaa_5$-$NHR_2$, the peptide is cyclic, wherein $R_1$ is Pap, $Xaa_1$ is Phe, $Xaa_2$ is Leu, $Xaa_3$ is Arg, $Xaa_4$ is Trp, Xaa is Tyr or His and $R_2$ is H or an alkyl group having between 1 and 5 carbons (SEQ ID NO: 4).

In certain embodiments, the synthetic peptides of the present invention are amidated linear peptides represented by the sequence $R_1$-$Xaa_1$-Gly-$Xaa_2$-$Xaa_3$-$Xaa_4$-$NHR_2$, wherein $R_1$ is Fmoc or FMS, $Xaa_1$ is Phe, $Xaa_2$ is Leu, $Xaa_3$ is Arg, $Xaa_4$ is Trp, and $R_2$ is H or an alkyl group having between 1 and 5 carbons (SEQ ID NO: 5).

According to certain embodiments, the synthetic peptide of the invention is a cyclic peptide of the sequence

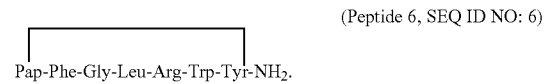

(Peptide 6, SEQ ID NO: 6)

According to certain embodiments, the synthetic peptide of the invention is a linear peptide of the sequence Fmoc-Phe-Gly-Leu-Arg-Trp-$NH_2$ (Peptide 8, SEQ ID NO: 8).

In certain embodiments, the saturated fatty acids from which the $C_5$-$C_{20}$ acyl is derived can be caprylic, capric, lauric, myristic, palmitic, stearic and arachidic acid, and the unsaturated fatty acids can be oleic acid, elaidic acid, linoleic acid, arachidonic acid and eicosapentaenoic acid.

According to certain embodiments, the analogs of Arg are selected from L-2-amino-3-guanidino propionic acid and N-ω,ω-dimethyl-L-arginine; the analogs of Trp are selected from beta-(3-benzothienyl)-L-Ala, 6-methyltryptophan, 5-methoxytryptophan, 5-hydroxytryptophan, 5-fluorotryptophan, 7-azatryptophpan, 5-bromotryptophan and 5-methyltryptophan; the analogs of Phe are selected from 2-fluorophenylalanine, 4-fluorophenylalanine, 4-bromophenylalanine, 2-chlorophenylalanine, L-homophenylalanine, 4-nitrophenylalanine and α-methylphenylalanine; and the analogs of Leu or Val are selected from t-butyl-L-alanine, L-cyclohexylglycine and L-cyclopentylglycine.

For the synthesis of the linear peptides of the invention, any method known in the art, such as the F-moc solid phase peptide synthesis technique, can be used.

The synthetic peptides of the invention may be in their free form or in the form of a salt or a chemical derivative thereof such as an ester. As used herein, the term "salts" refers to both salts of carboxyl groups and to acid addition salts of amino groups of the peptide molecule. Salts of a carboxyl group may be formed by means known in the art and include salts with inorganic salts, for example, sodium, calcium, ammonium, ferric or zinc salts, and the like, and salts with organic bases such as those formed for example, with amines, such as triethanolamine, arginine, or lysine, piperidine, procaine, and the like. Acid addition salts include, for example, salts with mineral acids such as, for example, hydrochloric acid or sulfuric acid, and salts with organic acids, such as, for example, acetic acid or oxalic acid. The esters may be formed by reacting suitable alcohols used in peptide chemistry with terminal carboxyl groups or with free non-terminal carboxyl groups of aspartic or glutamic acid residues.

As used herein, the phrase "Pharmaceutically acceptable" refers to a non-toxic, inert, and/or composition that is physiologically compatible with humans or other mammals.

According to the present invention, several modified Kp-10 derived peptides were prepared, in addition to the Peptides 6 and 8 of SEQ ID NOs: 6 and 8, respectively. The additional peptides have the sequences presented below, and were found not to have a significant effect in a paradigm for assessing early information processing in naïve mice, and therefore are used in the application for comparison only:

```
•Cys-Tyr-Asn-Trp-Asn-Ser-Phe-Gly-Leu-Arg-Phe-Cys-NH₂,Peptide 2, SEQ ID NO: 10
 └─────────────────────────────────────────────┘

•Cys-Phe-Gly-Leu-Arg-Trp-Cys-NH₂,Peptide 5,                SEQ ID NO: 12
 └──────────────────┘
•Fmoc-Tyr-Asn-Trp-Asn-Ser-Phe-Gly-Leu-Arg-Phe-NH₂,Peptide 7, SEQ ID NO: 13
```

Sensory gating is a largely automatic process by which the brain adjusts its response to stimuli. For example, when one stimulus is presented, there is a response; however, when the first stimulus is followed by a second stimulus soon after, the response to the second stimulus is blunted. This is an adaptive mechanism to prevent over stimulation that helps the brain focus on a stimulus among a host of other distracters, and contributes to the ability to selectively allocate attention to a significant event by silencing the background. The specific features of an individual's gating processes are viewed to be plastic, and governed by genetic and developmental processes, but also by environmental changes, neurochemical and hormonal state of the CNS. Sensory gating was shown to be disturbed in various disorders, including schizophrenia and Alzheimer.

Prepulse inhibition (PPI), the phenomenon by which a low-intensity prepulse stimulus attenuates the response to a subsequent startle-eliciting stimulus, is used as a measurement of the sensory gating function (Swerdlow and Geyer, 1998).

Figure 2:
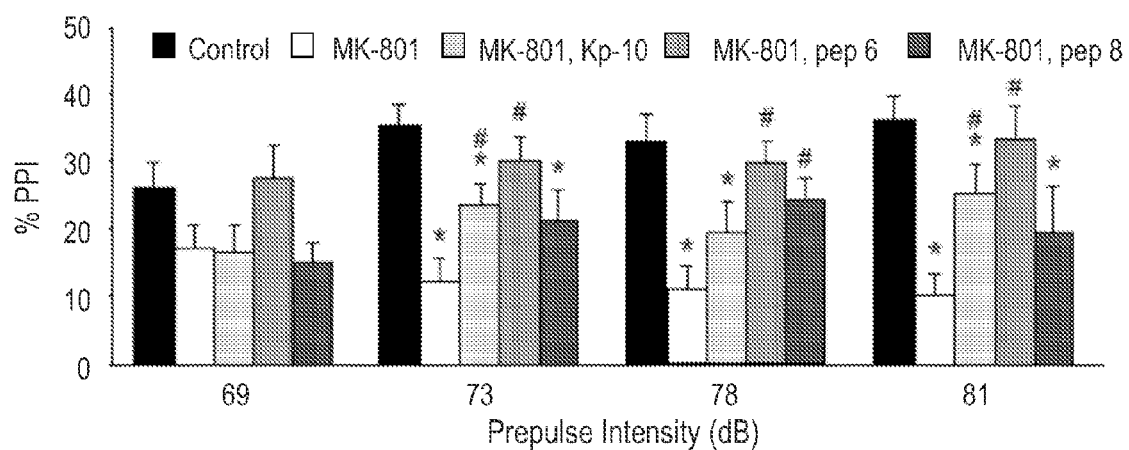
FIG. 2 shows the effect of Kp-10 (SEQ ID NO: 14) and the modified Kp-10 derived peptides 6 and 8 on PPI in mice treated with MK-801. C57BL/6J mice were injected with a peptide dissolved in DMSO and diluted in PBS to a final concentration of 0.2% (w/v) DMSO, MK-801 was injected after 15 min, and 15 min later measurement of the PPI was performed at 69, 73, 78 and 81 decibels. Mice were treated with (from left to right for each intensity): 0.2% DMSO in PBS (control, black bars, n=25), MK-801 alone (0.1 mg/kg, white bars, n=12), MK-801 and Kp-10 (13 μg/mouse, light gray bars, n=28), MK-801 and Peptide 6 (SEQ ID NO: 6, 8.75 μg/mouse, medium gray bars, n=16) or MK-801 and Peptide 8 (SEQ ID NO: 8, 8.75 μg/mouse, dark gray bars, n=14); Repeated measure ANOVA, F (4, 90)=8.6, P<0.0001; * indicates P<0.05, Fisher LSD post hoc analysis compared to control; # indicates P<0.05, Fisher LSD post hoc analysis compared to MK-801.

It has been found, in accordance with the present invention, that injecting mice treated with MK-801, which induces psychotic symptoms mimicking the effect of schizophrenia, with Peptide 6 (SEQ ID NO: 6) or Peptide 8 (SEQ ID NO: 8) of the invention, or with Kp-10 (SEQ ID NO: 14), which has previously been found to improve PPI in mouse models for schizophrenia, significantly improved PPI compared to animals treated only with MK-801. Furthermore, treatment with Peptide 6 restored PPI back to normal levels, having a greater effect than that of Kp-10, or of Peptide 8 (FIG. 2).

Figure 4A:
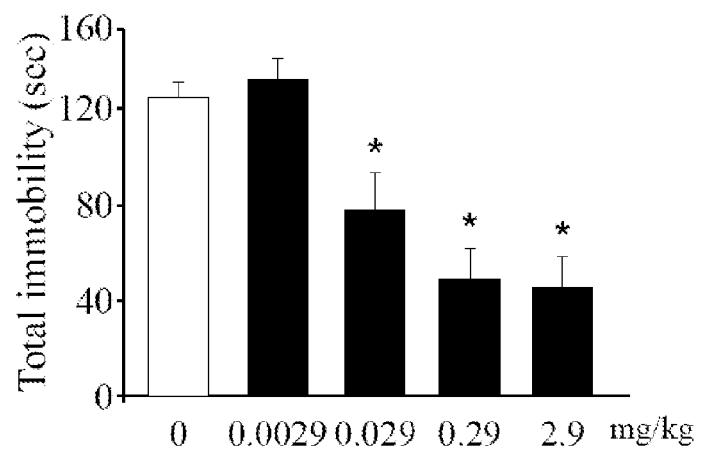
FIG. 4 shows the therapeutic effects and lack of side effects of Peptide 6 treatment. (A) Peptide 6 reduced the total immobility time in the tail suspension test in a dose dependent manner. From left to right: control (0.2% DMSO), 0.0029, 0.029, 0.29, 2.9 mg/kg of Peptide 6 (n=12/10/9/9/9, respectively, one way ANOVA, F (4,44)=11.3, P<0.0001). (B) PPI in mice treated with MK-801 and Risperidone, Olanzapine, or Peptide 6. From left to right: control (0.003N HCl and 0.2% DMSO, white bars), treated with MK-801 alone (light bray bars), and treated with a combination of MK-801 and Risperidone (MK-801+Ris at 0.1 mg/kg, medium gray bars), Olanzapine (MK-801+Ola at 0.375 mg/kg, dark gray bars) or Peptide 6 (MK-801+Pep6 at 0.29 mg/kg, black bars) (n=11/10/10/12/15, respectively, Repeated measure ANOVA, F (4,53)=2.7, P=0.03). (C) The effect of repeated injections of Peptide 6 on PPI at 69, 73, 78 and 81 decibels. Mice were injected intraperitoneally once a day during three days with 0.29 mg/kg of Peptide 6 and PPI was measured at the indicated intensities 30 minutes after the third injection. White bars: control (0.2% DMSO), black bars: Peptide 6. (n=18/16. Repeated measure ANOVA, F (1,32)=4.4, P=0.04). *P<0.05, Fisher LSD post hoc analysis. (D) The effect of treatment with Haloperidol, Olanzapine and Peptide 6 on duration of catalepsy. From left to right: control (0.003N HCl and 0.2% DMSO, white bar), treatment with Haloperidol (HAL-1 mg/kg, light gray bar), Olanzapine (OLA 0.375 mg/kg, and OLA 1.125 mg/kg, dark gray bars) and with Peptide 6 (Pep6 0.29 mg/kg, and Pep6 2.9 mg/kg, black bars), (n=7/6/7/7/7/6 respectively, *—one way ANOVA, F (5,34)=6.2, P=0.0003). (E) The effect of Haloperidol, Olanzapine and Peptide 6 on sedation. From left to right: control (0.003N HCl and 0.2% DMSO), and treated with Haloperidol (HAL-1 mg/kg), Olanzapine (OLA 0.375 mg/kg, OLA 1.125 mg/kg), and Peptide 6 (Pep6 0.29 mg/kg, Pep6 2.9 mg/kg). (n=8/7/8/7/8/7 respectively, one way ANOVA, F (5,39)=4.3, P<0.0001). (F) The effect of Haloperidol, Olanzapine and Peptide 6 on spontaneous activity in the open field. Distance—total distance in meters moved within the field. From left to right: control (0.003N HCl and 0.2% DMSO, white bar), Haloperidol (HAL-1 mg/kg, light bray bar), Olanzapine (OLA 0.375 mg/kg, OLA 1.125 mg/kg, dark gray bars), and Peptide 6 (Pep6 0.29 mg/kg, and Pep6 2.9 mg/kg, black bars). (n=6/6/7/7/6/7 respectively, one way ANOVA, F (5,32)=17.8, P<0.0001). (G) The effect of Haloperidol, Olanzapine and Peptide 6 on forced activity measured as the time in seconds required for each mouse to fall from a rotarod. From left to right: control (0.003N HCl and 0.2% DMSO, white bar), Haloperidol (HAL-1 mg/kg, gray bar), Olanzapine (OLA 0.375 mg/kg, OLA 1.125 mg/kg, light gray bars), and Peptide 6 (Pep6 0.29 mg/kg, and Pep6 2.9 mg/kg, black bars). (n=7/6/7/7/7/6 respectively, one way ANOVA, F (5,34)=6.3, P=0.0003). * indicates P<0.05, Fisher LSD post hoc analysis compared to control; # indicates P <0.05, Fisher LSD post hoc analysis compared to MK-801.
Figure 4B:
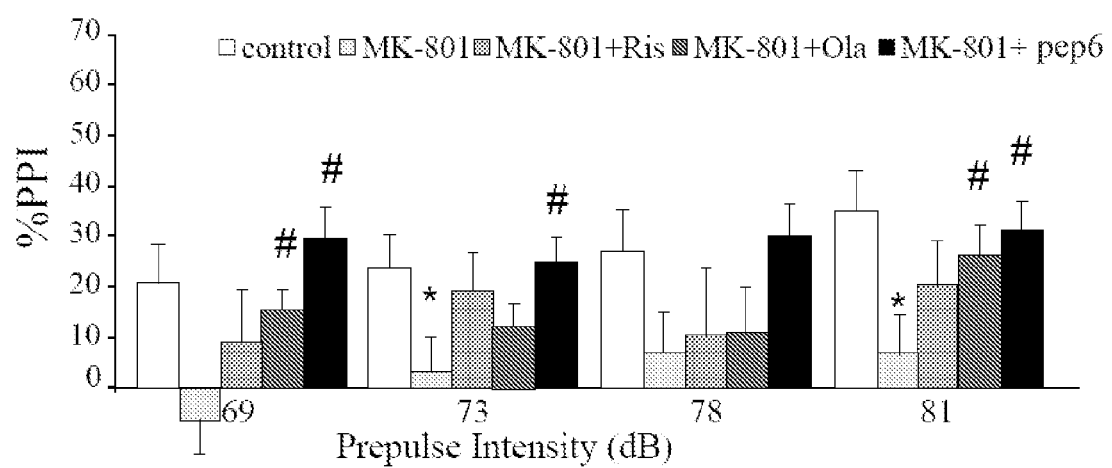

It has additionally been found, in accordance with the present invention, that the effect of Peptide 6 on PPI in the MK-801 schizophrenia mouse model is greater than that of known antipsychotic drugs—Risperidone and Olanzapine (FIG. 4B). Additionally, Peptide 6 did not have side effects typical to the anti-psychotic drugs such as Haloperidol and Olanzapine (FIGS. 4D-4G).

The present invention thus provides a synthetic peptide of the invention as defined above or a pharmaceutically acceptable salt thereof, for use as a medicament.

The present invention further provides a pharmaceutical composition comprising a peptide of the invention as defined above or a pharmaceutically acceptable salt thereof and a pharmaceutically acceptable carrier.

PPI deficits are not unique to a single form of psychopathology. In addition to schizophrenia, impairment of PPI has been reported in several diseases such as autistic disorder, Huntington's chorea, obsessive-compulsive disorder, attention deficit hyperactivity disorder (ADHD), Tourette's syndrome, and some cases of Alzheimer's disease (Castellanos et al. 1996; Ornitz et al. 1992; Perry et al., 2007; Swerdlow et al. 1993; Swerdlow et al. 1995; Ueki et al., 2006). Therefore, PPI is often used as a paradigm, for assessing the modulation of early information processing and is widely used to investigate antipsychotic drug action in animals.

Thus, according to certain embodiments, the synthetic peptides of the invention are useful for treating a disease or disorder presenting behavioral abnormalities associated with impairment of sensory gating function. According to certain embodiments, such diseases are schizophrenia, autistic disorder, Huntington's chorea, obsessive-compulsive disorder, attention deficit hyperactivity disorder (ADHD) or Tourette's syndrome. According to a certain embodiment, the disease is schizophrenia. In certain embodiments, the synthetic peptide has a sequence as set forth in SEQ ID NO: 6. In certain embodiments, the synthetic peptide has a sequence as set forth in SEQ ID NO: 8.

The phrase "disease or disorder presenting behavioral abnormalities associated with impairment of sensory gating function" is used herein to relate to any disease or disorder in which any association with impaired sensory gating as described above, such as for example, impaired PPI, has been found.

Figure 6:
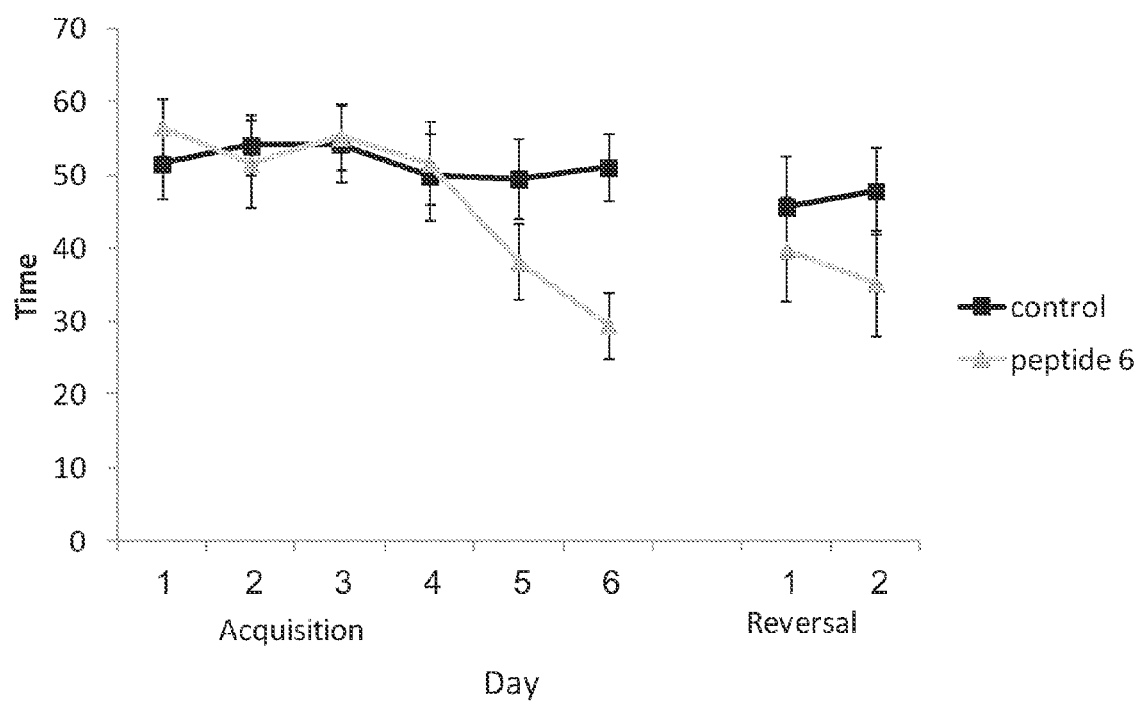
FIG. 6. Effect of Peptide 6 on performance of the Alzheimer mouse model 5XFAD mice in the Morris water maze. The Y axis is the time in seconds which took the mouse to reach the platform in each day of the experiment. Data in each day is the average of all trials in this day (n=8/8 respectively, Repeated measure ANOVA, F (1,13)=4.6, P<0.05). Black squares—control (0.1% DMSO), gray triangles—mice treated with Peptide 6. The Acquisition and the Reversal phases are described in the experimental section. The bars in each point represent standard error.

It has further been found, in accordance with the present invention, that Peptide 6 improves spatial learning and memory in the Morris Water Maze in a mouse model for Alzheimer's disease (FIG. 6).

According to certain embodiments, the synthetic peptides of the invention may be used for treating Alzheimer's disease. According to a certain embodiment, the synthetic peptide is Peptide 6.

Figure 1B:
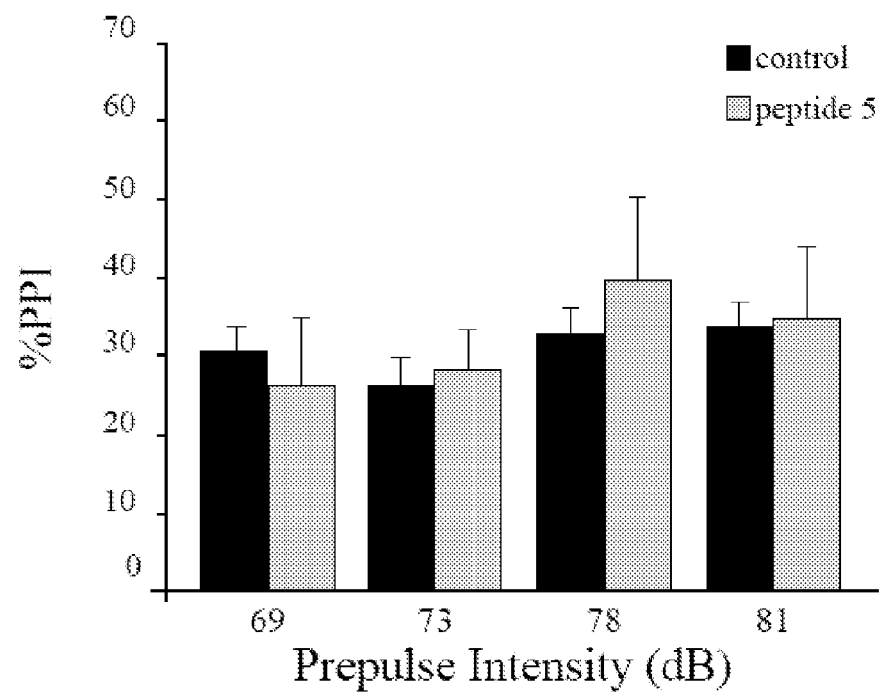
Figure 1C:
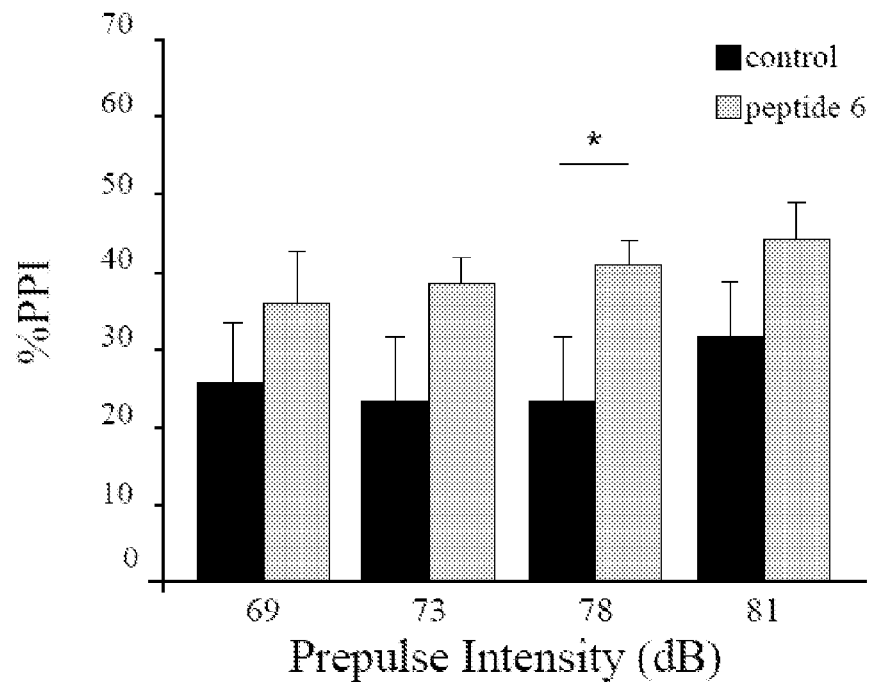
Figure 3:
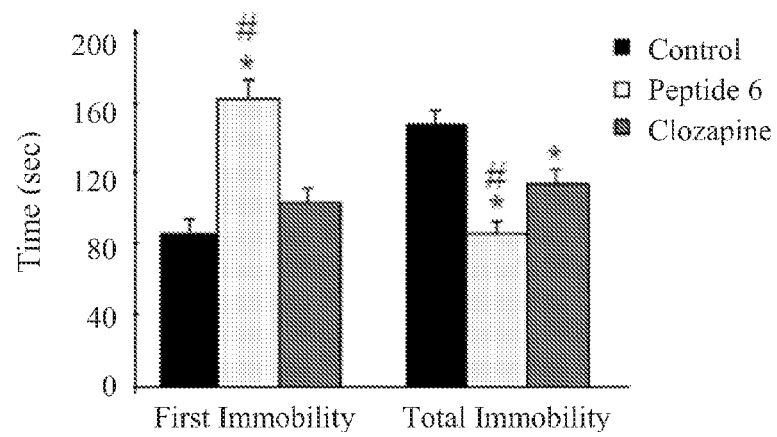
FIG. 3 shows the anti-depressive effect of Peptide 6 (SEQ ID NO: 6) in comparison with Clozapine. Mice were treated with (left to right): 0.003N HCl and 0.2% DMSO (control, black bars, n=8), Peptide 6 (8.75 μg, light gray bars, n=7), or Clozapine (0.3 mg/kg, dark gray bars, n=6), and subjected to a tail suspension test. Peptide 6 increased latency time until the first occurrence of immobility (First Immobility, ANOVA, F (2, 18)=10.8, P=0.0008) and reduced the total duration of immobility (Total Immobility, ANOVA, F (2, 18)=3.95, P=0.039). * indicates P<0.05, Fisher LSD post hoc analysis compared to control; # indicates P<0.05, Fisher LSD post hoc analysis compared to Clozapine treatment.
Figure 4C:
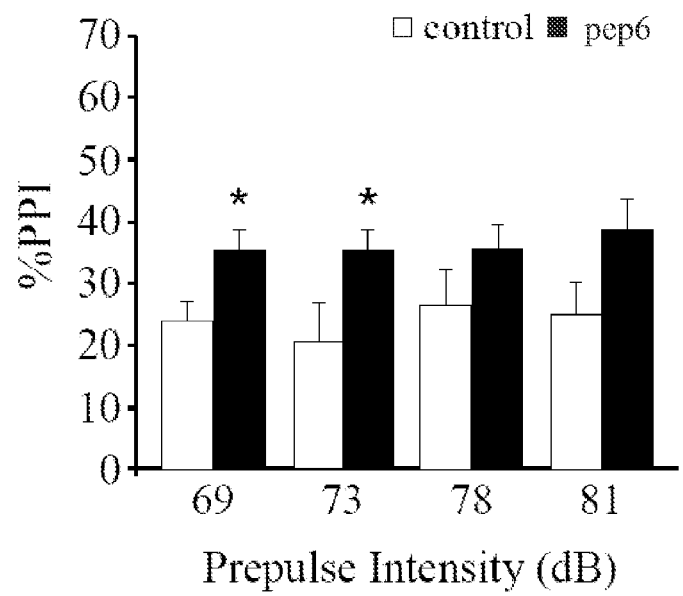

It has further been shown, in accordance with the present invention, that Peptide 6 has an anti-depressive effect in the tail suspension test in Naïve animals, (FIGS. 3 and 4A), and that effect was higher than that of the known anti-psychotic drug clozapine. Peptide 6 additionally has been found to have an effect of increasing PPI in Naïve animals (FIGS. 1C and 4C).

Thus, according to certain embodiments, the synthetic peptides of the invention may be used for treating depression and/or cognitive impairment. According to a certain embodiment, the synthetic peptide is Peptide 6.

Depression as well as cognitive impairment are among the known symptoms of schizophrenia and of Alzheimer's disease.

Thus, according to certain embodiments, the synthetic peptides of the invention may be used for treating depression and/or cognitive impairment associated with schizophrenia or with Alzheimer's disease.

In certain embodiments, the synthetic peptides of the invention may be used for treating depression and/or cognitive impairment associated with diseases other than schizophrenia and Alzheimer's disease.

In certain embodiments, the peptide is Peptide 6, having a sequence as set forth in SEQ ID NO: 6.

According to certain embodiments, the pharmaceutical compositions of the invention may comprise a single synthetic peptide of the invention or more than one synthetic peptides of the invention.

The pharmaceutical compositions of the present invention may be prepared by conventional techniques, e.g. as described in Remington: The Science and Practice of Pharmacy, 19$^{th}$ Ed., 1995. The composition may be in solid, semisolid or liquid form or it can be designed for slow release of the peptide. According to certain embodiments, the compositions of the invention may be further mixed with excipients such as stabilizers, flavoring agents, antiseptics, binders, antioxidants, etc.

As used herein, a "pharmaceutically acceptable carrier" is a pharmaceutically acceptable solvent, suspending agent or vehicle, for delivering the instant compounds to the patient. The carrier may be liquid or solid and is selected with the planned manner of administration in mind. Liposomes can also be a pharmaceutical carrier.

The present invention further provides a method for the treatment of a disease or disorder presenting behavioral abnormalities associated with impairment of sensory gating function, depression or cognitive impairment, comprising administering to a patient in need thereof an effective amount of a synthetic peptide of the invention or a pharmaceutically acceptable salt thereof.

According to certain embodiments, the disease is schizophrenia. According to certain embodiments, the disease is Alzheimer's disease. According to certain embodiments, the synthetic peptide is Peptide 6.

As used herein, the phrase "effective amount" or "therapeutically effective amount" refers to the quantity of a component that is sufficient to yield a desired therapeutic response without undue adverse side effects (such as toxicity, irritation, or allergic response) commensurate with a reasonable benefit/risk ratio when used in the manner of this invention.

As used herein, the term "treatment" includes ameliorating, alleviating, attenuating and/or even abolishing symptoms associated with the disease or disorder. In case of schizophrenia, it is contemplated by the invention that the treatment with the synthetic peptides of the invention will ameliorate/alleviate the psychotic and/or depression symptoms associated with the disease and/or will improve the cognitive functions impaired in the schizophrenic patient.

According to certain embodiments, the treatment of schizophrenia comprises administration of a peptide of the invention or a pharmaceutically acceptable salt thereof alone or in combination with one or more drugs suitable for treatment of schizophrenia such as clozapine, amisulpride, olanzapine, risperidone, quetiapine, ziprasidone, aripiprazole or paliperidone.

According to certain embodiments, the treatment of Alzheimer's disease comprises administration of a peptide of the invention or a pharmaceutically acceptable salt thereof alone or in combination with one or more drugs suitable for treatment of Alzheimer's disease such as acetylcholinesterase inhibitors (e.g. tacrine, rivastigmine, galantamine and donepezil) or NMDA receptor antagonists such as memantine, or first generation antipsychotics such as Chlorpromazine, Haloperidol, Perphenazine, Fluphenazine.

Any suitable composition and route of administration is encompassed by the invention, including oral (e.g. in the form of tablets, capsules, microcapsules, and the like), parenteral (e.g., in the form of subcutaneous, intramuscular, intraarticular, or intravenous injection), inhalation, intranasal (in the form of sprays), intrathecal, intraperitoneal, intradermal, transdermal or other known routes of administration suitable for the administration of peptides to human beings.

According to certain embodiments, the peptides of the invention are administered by oral administration.

The dose of the peptide to be administered will be determined by the competent physician and will depend on the agent used, the severity of the disease, the age, and the weight of the patient, and may vary from 0.1-100 mg, preferably 1.0-50 mg, more preferably 1.0-20 mg for oral application; or from 0.01-30 mg, preferably 1.0-30 mg, more preferably 1.0-20 mg for parenteral application; or from 0.01-10 mg, preferably 0.05-5 mg, more preferably 0.05-0.2 mg for intravenous (IV) application.

The invention will now be illustrated by the following non-limiting Examples.

EXAMPLES

Materials and Methods

Unless otherwise indicated, Peptide 6 (cKp-7, Pap-Phe-Gly-Leu-Arg-Trp-Tyr-NH$_2$, Pap=p-aminophenylalanine; the Pap and the Tyr are connected in an internal azo-bridge, to yield a cyclic peptide (GL Biochem (Shanghai) Ltd.)) was dissolved in DMSO and diluted in PBS to a final concentration of 0.1% DMSO, and 100 µl were injected intraperitoneally at the indicated dose 30 min before the behavioral analysis.

Risperidone (Sigma, Israel) was dissolved in 0.06N HCL and administered intraperitoneally at a dose of 0.1 mg/kg in a final concentration of 0.003N HCL, 0.1% DMSO, 30 min prior to the PPI analysis.

Olanzapine (Sigma, Israel) was dissolved in 0.06N HCL and administered intraperitoneally at a dose of 0.375 or 1.125 mg/kg in a final concentration of 0.003N HCL, 0.1% DMSO, 30 min prior to the behavior analysis.

Haloperidol (Sigma, Israel) was dissolved in 0.06N HCL and administered intraperitoneally at a dose of 1 mg/kg in a final concentration of 0.003N HCL, 0.1% DMSO, 30 min prior to the behavior analysis.

Animals.

Inbred 12-16 week old C57B1/6 mice were supplied by the Animal Breeding Center of the Weizmann Institute of Science. Since the estrous cycle affects PPI, male mice were used in all experiments unless otherwise indicated. All animals were handled according to the regulations formulated by the Weizmann Institute's Animal Care and Use Committee and maintained in a pathogen free environment.

Kp-10 Peptide.

Kisspeptin-10 (Kp-10, human Metastin amino acids 45-54, YNWNSFGLRF-NH$_2$ (SEQ ID NO: 14), Weizmann Peptide Facility or Sigma-Aldrich, Israel) was injected intraperitoneally at a dose of 13 µg/mouse dissolved in PBS, 30 min before the PPI analysis. MK-801 (Sigma) was used at 0.1 mg/kg and administered 15 min prior to the PPI analysis.

Acoustic Startle Response (Prepulse Inhibition, PPI) Testing.

Acoustic startle response testing was performed within startle chambers purchased from Med Associates, Inc. (Med Associates, St. Albans, Vt., USA), as described in Cardon et al., 2010. During a period of acclimation, a 65-decibel (dB) background noise was presented for 5-min, and continued throughout the test session. All sessions for testing of acoustic startle response consisted of startle trials (pulse alone, 40-milliseconds (ms), 120-dB), prepulse trials (prepulse 20-ms, 69, 73, 78, or 81 dB followed by a [100-ms delay] pulse), and no-stimulus trials. All sessions were presented in pseudo-random order. The average time between trials was 15 seconds (range 12-30 seconds). Startle response was calculated from the reaction to the first pulse-alone trial.

Calculation of Prepulse Inhibition (PPI).

PPI was calculated as: % PPI=100−{[(startle response for prepulse+pulse)/(startle response for pulse-alone)]×100}. Reduced PPI indicates schizophrenia-related behavior. No difference between Kp-10 and PBS treated mice was observed in the startle response and in the prepulse-alone trials, in which the response was negligible compared to the pulse trials.

Tail Suspension Test.

The tail suspension apparatus was made of horizontal metal rod supported by a stand. Each mouse was suspended from its tail using adhesive tape, suspending each mouse individually. The immobility time was measured during a 6 min observation period, latency to first immobility and total immobility is calculated.

Open-Field Test.

The open-field apparatus consisted of a white Plexiglas box (40×40×30 cm) with 16 squares (10×10 cm) painted on the floor (12 outer and 4 inner). Each mouse was placed in the center of the apparatus to initiate a 15-min test session. The number of entrances to the inner squares, time (min) spent in the inner squares, and total distance moved within the field (cm) were monitored.

Radial Arm Water Maze (RAWM).

Mice were tested for two days on 6 radial arm water maze paradigm in a water pool, as described in Alamed et al. (2006). Briefly, mice received injection of a peptide of the invention in the beginning of each day. On the first day, 15 trials were performed, in trials 1, 3, 5, 7, 9 and 11 the platform was visible, and in all other trials the platform was hidden. On the second day, 12 trials were performed, all of them with hidden platform. The time required to reach the platform and the number of errors (incorrect arm entries) in 1-min time period was recorded.

Morris Water Maze (MWM) Test.

Acquisition phase: mice were given 3-4 trials per day on 6 consecutive days. In each trial they were required to find a hidden platform located 1.5 cm below the water surface in a pool 1.4 m in diameter. Within the testing room, only distal visuo-spatial cues for location of the submerged platform were available. The escape latency, i.e., the time required by the mouse to find the platform and climb onto it, is recorded for up to 60 s. Each mouse is allowed to remain on the platform for 20 s and is then moved from the maze to its home cage. If the mouse does not find the platform within 60 s, it is placed manually on the platform and returned to its home cage after 20 s. The interval between trials was 600 s. On day 6 each mouse was tested by a probe trial: the platform was removed from the pool and the location of each mouse in the pool was followed for 60 sec. For the reversal phase, mice were given four trials per day on 2 consecutive days, and the platform was at a different location. Data were recorded using an EthoVision automated tracking system (Noldus).

Catalepsy and Sedative Effect.

Catalepsy is a state of immobility, and was measured by means of the bar test. The forepaws of the animal were placed on a bar (0.75 cm in diameter and 5 cm above the floor) and the latency until the mouse moved the forepaws off the bar was measured.

Sedative effect was evaluated by observing the mice and scoring their sedative state as follows: 0, spontaneous movement; 1, mild intermittent spontaneous movement; 2, severe intermittent spontaneous movement; 3, no spontaneous movement; 4, loss of auditory reflex; 5, loss of corneal reflex; 6, loss of response to tail pinch.

Forced Activity (Rotarod) was analyzed using the Rotarod apparatus (Jones and Roberts 7650, Ugo Basile, Italy). Animals were placed on an accelerating rod, and time required for each mouse to fall from the rod was recorded. Out of three trails, the longest time taken for an animal to fall from the rod was recorded and used for analysis.

Example 1

Synthesis of Modified Kp-10 Derived Peptides

Linear Peptides 8 (SEQ ID NO: 8), and linear Peptide 4 (SEQ ID NO: 7) which is a precursor of cyclic Peptide 6 having the same sequence (SEQ ID NO: 6), were synthesized by the solid-phase method using an Advanced Chemical APEX 396 multiple peptide synthesizer (Louisville, Ky.) following the commercial protocol recommended by the manufacturer for the Fmoc-strategy. After completion of peptide chain assembly, Peptide 4 was deprotected and cleaved from the polymeric support (Rink amide) with a mixture of trifluoroacetic acid (TFA), thioanisol triethylsilane and water (85:5:5:5 v/v) at room temperature for 3 hours. Peptide 8 was cleaved from the polymeric carriers while leaving the N-terminal Fmoc-protection intact. The crude peptides, following precipitation with t-butylether, were purified by HPLC (to >95%).

Peptide 4 was cyclized to form an internal azo-bond between the Pap and Tyr residues, following reaction with an equimolar amount of nitrous acid ($HNO_2$) at acidic pH ∼1 at 0° C., and cyclization at high dilution (1 mg/2 ml) upon adjustment of the pH to 8, thereby obtaining Peptide 6. The cyclization was nearly quantitative. Final purification (>95%) by HPLC led to the desired cyclic product as revealed by mass spectrometry and amino acid analysis. The cyclization procedure was according to Fridkin et al., 2006 and Fridkin et al., 2011.

Linear Peptides 1 and 3 (SEQ ID NOs: 9 and 11, respectively), having the same sequence as cyclic Peptides 2 and 5, respectively, were synthesized by the solid-phase method as described above, and titrated with potassium ferrocyanide, in a solution of ammonium acetate pH 7 to form the corresponding cystine (S—S) cyclic Peptides 2 and 5 (SEQ ID NOs: 10 and 12, respectively).

Peptide 7 (SEQ ID NO: 13) was synthesized as described above for Peptide 8.

Example 2

Modified Kp-10 Derived Peptides Improve PPI in Naïve Mice

To determine the effect of the Kp-10 derivatives on behavior, we studied the effect of each of the peptides 2, 5, 6, 7 and 8 on PPI.

To test Peptide 2 (SEQ ID NO: 10), the peptide was dissolved in DMSO and then diluted in PBS to a final concentration of 1% (w/v) DMSO. Male C57B1/6J naïve mice were injected intraperitoneally with 15 μg of the peptide or with 1% DMSO in PBS (control). Prepulse intensity analysis was performed after 30 minutes at 69, 73, 78 or 81 decibels. As can be seen from FIG. 1A, Peptide 2 slightly improved the % PPI relative to controls, however, the effect was not significant (Repeated measure ANOVA, F (degrees of freedom) (1,18)=4.2, P=0.06).

To test Peptide 5 (SEQ ID NO: 12), mice were similarly injected with 8.3 μg Peptide 5 in 1% DMSO in PBS or with 1% DMSO in PBS (control). Prepulse intensity analysis was performed after 30 minutes at 69, 73, 78 or 81 decibels. As can be seen from FIG. 1B, Peptide 5 slightly improved the % PPI at 73, 78 and 81 decibels relative to controls, however, the effect was not significant (Repeated measure ANOVA, F (1, 12)=0.1, P=0.7).

To test Peptide 6 (SEQ ID NO: 6), mice were injected with 8.75 μg Peptide 6 in 1% DMSO in PBS or with 1% DMSO in PBS (control). Prepulse intensity analysis was performed after 30 minutes at 69, 73, 78 or 81 decibels. As can be seen from FIG. 1C, Peptide 6 strongly elevated the % PPI at all intensities relative to controls, and this effect was significant at 78 decibels (Repeated measure ANOVA, F (1, 19)=4.7, P=0.047*P<0.05, Fisher LSD post hoc analysis).

Figure 1D:
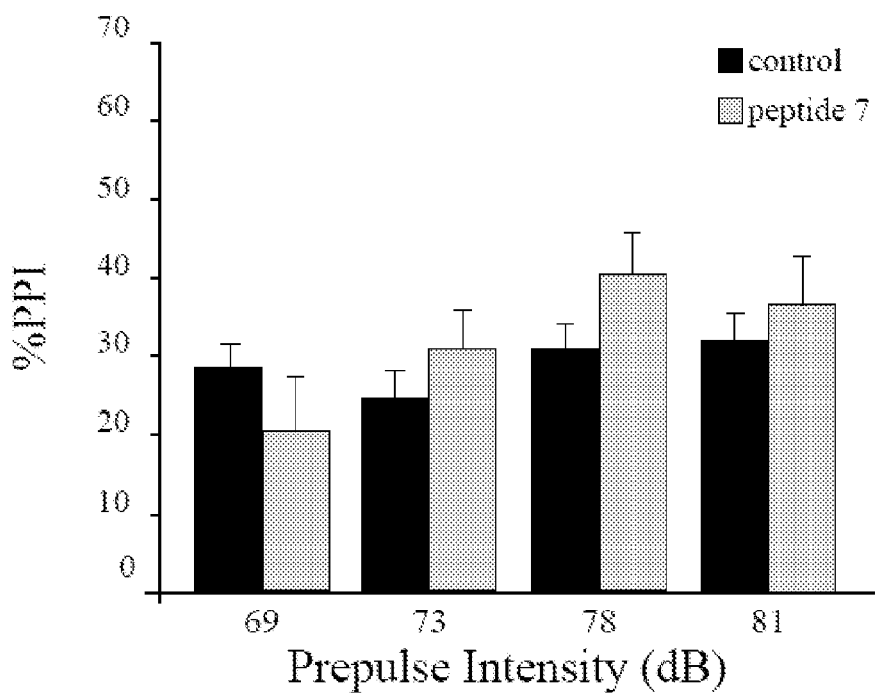

To test Peptide 7 (SEQ ID NO: 13), mice were injected with 15.3 μg Peptide 7 in 1% DMSO in PBS or with 1% DMSO in PBS (control). Prepulse intensity analysis was performed after 30 minutes at 69, 73, 78 or 81 decibels. As can be seen from FIG. 1D, Peptide 7 slightly improved the % PPI at 73, 78 and 81 decibels relative to controls, however, the effect was not significant (Repeated measure ANOVA, F (1, 18)=1.15, P=0.3).

Figure 1E:
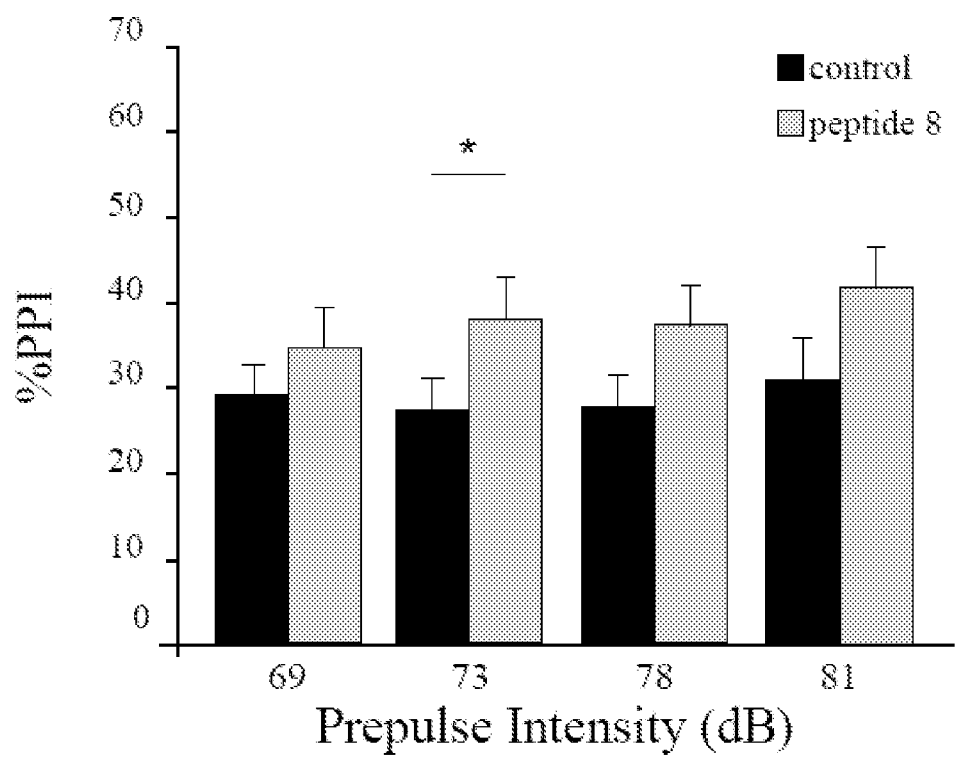

To test Peptide 8 (SEQ ID NO: 8), mice were injected with 8.75 μg Peptide 8 in 1% DMSO in PBS or with 1% DMSO in PBS (control). Prepulse intensity analysis was performed after 30 minutes at 69, 73, 78 or 81 decibels. As can be seen from FIG. 1E, Peptide 8 strongly elevated the % PPI at all intensities relative to controls, and this effect was significant at 73 decibels (Repeated measure ANOVA, F (1, 31)=5.3, P=0.028*P<0.05, Fisher LSD post hoc analysis).

To summarize, as can be seen from FIGS. 1A-1E, while treatment with Peptides 2, 5 and 7, did not significantly improve the PPI response relative to untreated animals, administration of Peptides 6 and 8 resulted in a significant increase in % PPI at all intensities.

Example 3

Modified Kp-10 Derived Peptides Protect Against PPI Dysfunction in an Animal Model for Schizophrenia To determine if the peptides that most strongly affect PPI in naïve mice (Peptides 6 and 8) can abolish psychotic symptoms in a drug induced animal model of schizophrenia, we analyzed their effect on PPI in the MK-801 model. MK-801 (an antagonist of the N-methyl-D-aspartate (NMDA) receptor channel) acts as a psychomimetic agent, inducing psychotic symptoms that mimic the cognitive impairment and behavioral abnormalities associated with schizophrenia.

The neurotransmitter imbalance induced by MK-801 causes PPI dysfunction, one of the characteristic features of patients with schizophrenia. In an experiment depicted in FIG. 2, C57BL/6J mice were injected with Kp-10 (13 μg/mouse, light gray bars), or with Peptides 6 (8.75 μg/mouse, medium gray bars) or 8 (8.75 μg/mouse, dark gray bars) dissolved in DMSO and then diluted in PBS to a final concentration of 0.2% (w/v) DMSO; the control group received 0.2% DMSO in PBS (black bars). After 15 min, MK-801 (0.1 mg/kg) was injected; 15 min later, measurement of the PPI was performed. As expected, in mice injected with MK-801 (white bars), the PPI response was reduced compared to the PBS injected control. All three treatments (Kp-10, Peptide 6 and Peptide 8) significantly improved PPI compared to the MK-801 treated animals (FIG. 2, repeated measure ANOVA, F (4, 90)=8.6, P>0.0001; # indicates P<0.05, Fisher LSD post hoc analysis compared to MK-801). However, only Peptide 6 restored PPI back to normal levels (* in FIG. 2 indicates P<0.05, Fisher LSD post hoc analysis compared to control, no significant difference at all prepulse intensities found between no MK-801 controls and treatment with Peptide 6); Kp-10 and Peptide 8 improved PPI after MK-801 administration but did not abolish its affect, and PPI in these groups remained significantly different from that of the control group. Thus, peptide 6 is more effective in abolishing the effect of MK-801 on PPI than either Peptide 8 or Kp-10.

Example 4

Antidepressive Effect of Modified Kp-10-Derived Peptides

Schizophrenia patients suffer from cognitive and negative symptoms (e.g., depression) in addition to psychotic symptoms. Kp-10 was shown to elevate BDNF mRNA levels in hippocampal slices (Arai et al., 2009), and was further shown in WO 2010/137022 to have an antidepressant effect by the tail suspension test, an established method for screening antidepressant-like activity in mice (Steru et al., 1985; Cryan et al., 2005).

Peptide 6 of the invention was tested for an antidepressive effect by the tail suspension test as follows: Naïve mice were treated with Peptide 6 of the invention (8.75 μg of peptide dissolved in DMSO and then diluted in PBS to a final concentration of 0.2% DMSO (w/v), HCL was added to a final concentration of 0.003N) or with Clozapine (0.3 mg/kg dissolved in 0.3N HCL diluted in PBS to a final concentration of 0.003N HCL, DMSO was added to a final concentration of 0.2% DMSO (w/v)) and subjected to the tail suspension test, in which the mouse was suspended by the tail from a lever, and the movements of the animal were recorded. As can be seen in FIG. 3, treatment with Peptide 6 (light gray bars) significantly increased latency until the first occurrence of immobility compared with the control (black bars) and with Clozapine (dark gray bars) (ANOVA, F (2, 18)=10.8, P=0.0008) and significantly reduced the total duration of immobility (ANOVA, F (2, 18)=3.95, P=0.039) compared with the control and with Clozapine treatment. These results indicate that Peptide 6 of the invention can be used as an antidepressant and that it has a higher antidepressive activity than the antipsychotic drug Clozapine.

Example 5

Therapeutic Effects and Lack of Side Effects of Peptide 6

To determine the dose effect of Peptide 6 we injected it in increasing dosages and analyzed its effect on tail suspension test. Peptide 6 reduced the total immobility time in a dosage dependent manner, at 0.029, 0.29 and 2.9 mg/kg (FIG. 4A).

This result showed that Peptide 6 has a wide therapeutic range. A dose of 0.29 mg/kg is equivalent to the dose used for Kp-10, which reduced the total immobility in the tail suspension test (FIG. 10C of WO 2010/137022).

We further analyzed the effect of Peptide 6 on the reduction in PPI induced by MK-801 in comparison with the common antipsychotics Risperidone and Olanzapine. Both of these drugs cause sedative effects, and since PPI cannot be measured correctly in sedated mice we first evaluated the highest dose of the drugs that can be injected to the mice without causing sedative effects: the chosen dose was 0.1 mg/kg for Risperidone and 0.375 mg/kg for Olanzapine (data not shown). As can be seen from FIG. 4B, all drugs elevated PPI in the MK-801 treated mice, but only Peptide 6 (black bars) completely overcame the effect of MK-801 and restored the PPI levels to control level (white bars). ANOVA of percent PPI indicated a significant main effect of the treatments, but not of the prepulse intensities. One-way ANOVA analysis of single intensities revealed statistically significant differences between treatments at prepulse intensities of 69, 73 and 81 dB.

The effect of repeated injections of Peptide 6, was tested by injecting 0.29 mg/kg of Peptide 6 once a day during three days and measuring PPI 30 minutes after the third injection. As can be seen from FIG. 4C, repeated injections of Peptide 6 increased the PPI at all intensities, the effect was significant at PPI of 69 and 73 decibels.

To evaluate the potential side effect of Peptide 6 we analyzed its effect on catalepsy, sedative effect, and effect on spontaneous (open field) and forced (rotarod) activity as compared with the antipsychotics Haloperidol (1 mg/kg) and Olanzapine (0.375 and 1.125 mg/kg).

Figure 4D:
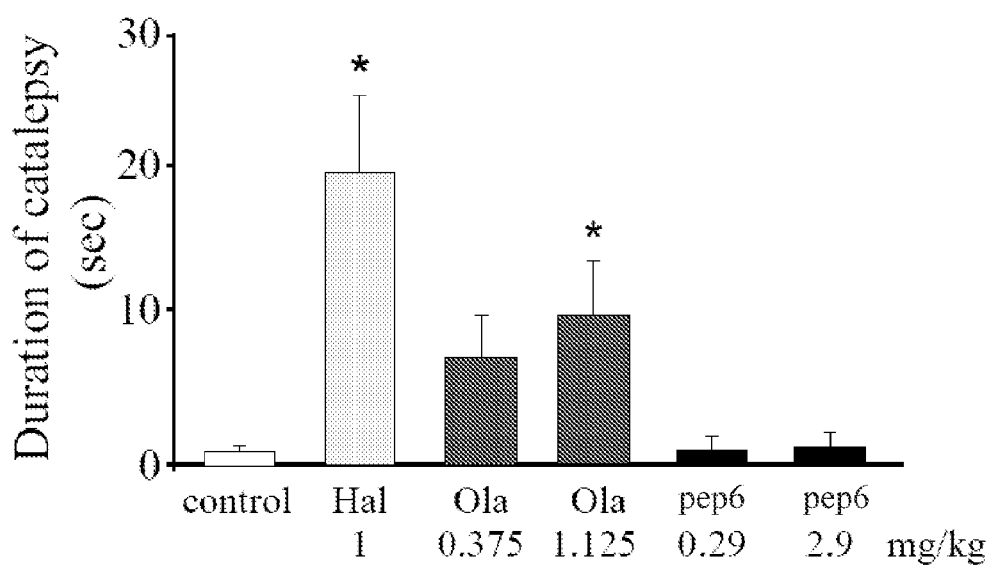

Halperidol (light gray bar, HAL) and Olanzapine (dark gray bars, OLA at 0.375 and 1.125 mg/kg) both had catalepsy effects even at low levels of Olanzapine, on the other hand, Peptide 6 (black bars, Pep6 at 0.29 and 2.9 mg/kg) did not have catalepsy effect at either dosage tested (FIG. 4D).

Figure 4E:
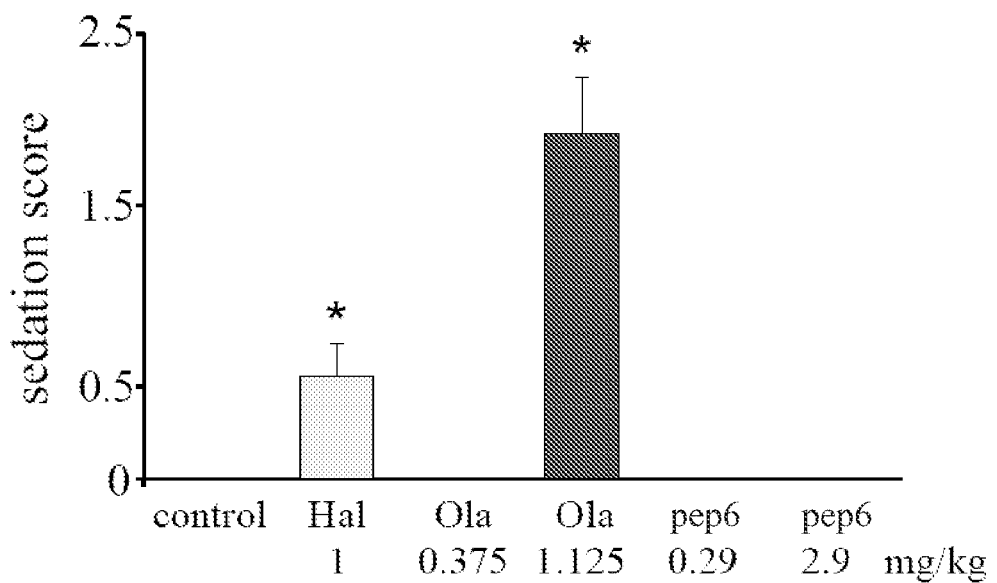

Next we analyzed the sedative effects of Haloperidol, Olanzapine and Peptide 6. Sedative effect was evaluated by observing the animal using a sedative score. Haloperidol had low sedative effect, Olanzapine had sedative effect at a dose of 1.125 mg/kg, Peptide 6 did not have a sedative effect at either of the two dosages tested (FIG. 4E).

Figure 4F:
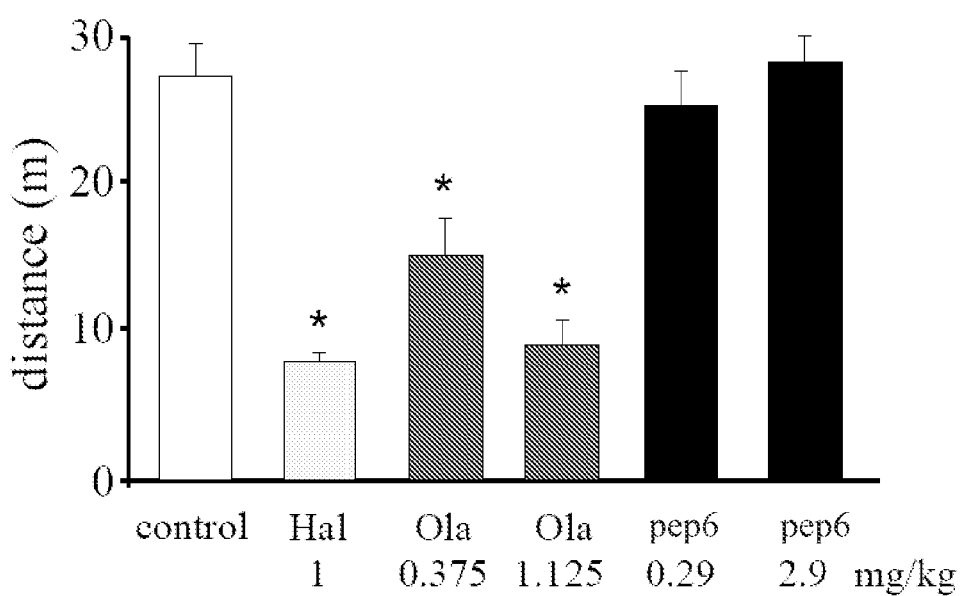
Figure 4G:
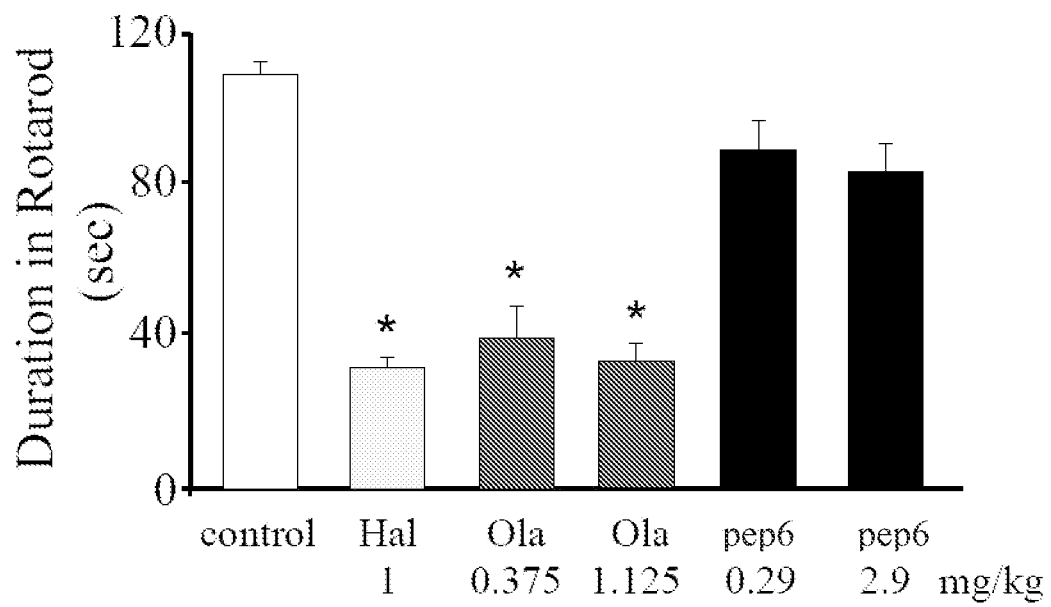

Regarding spontaneous and forced activity, Haloperidol (HAL, 1 mg/kg, light gray bar) and Olanzapine (OLA 0.375 and OLA 1.125 mg/kg, dark gray bars) reduced mice activity both in the open field (spontaneous) and in the Rotarod (forced), while Peptide 6 (Pep6 at 0.29 and 2.9 mg/kg, black bars) did not affect activity level in either of the tests at either dosage tested (FIGS. 4F,G). These results showed that Peptide 6 has no motor side effect compared to other antipsychotic drugs.

Example 6

Figure 5:
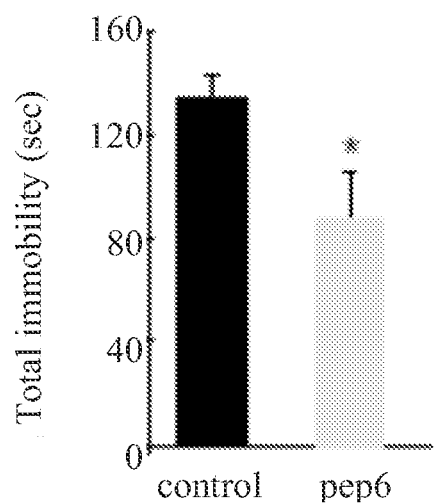
FIG. 5. Peptide 6 administered orally reduces total immobility in a tail-suspension test. 2.9 mg/kg of Peptide 6 in 100 μl water with 1% DMSO was administrated to naïve wild-type mice by oral gavage and the mice were tested by a tail-suspension test (TST) 30 min later. Black bars: control; white bars: peptide 6 (n=10/12 for control and test; * indicates P<0.02 by t-test).

Peptide 6 Administered Orally Reduces Total Immobility in a Tail-Suspension Test 2.9 mg/kg of Peptide 6 were dissolved in DMSO and then diluted in water to a final concentration of 1% DMSO. 100 µl was administrated to naïve wild-type mice by oral gavage and the mice were tested by a tail-suspension test (TST) 30 min later. Control mice received 100 µl water with 1% DMSO. As can be seen from FIG. 5, Peptide 6 significantly reduced the total immobility relative to the control.

Example 7

Plasma Stability of Peptide 6

1 µM Peptide 6 was dissolved in human plasma, and peptide concentration was analyzed by HPLC after 0, 0.5, 1, 1.5, 2 h of incubation. The assay was performed by Cerep, Inc (Redmond, Wash., U.S.A). As presented in Table 1, Peptide 6 is highly stable, with a calculated half-life of >120 minutes. Peptide 6 exhibits increased stability, with 94% of the original material remained in the human plasma after 60 min, relative to Kp-10, which was below detectable level after 60 min (chan, et al., 2011, Kisspeptin resets the hypothalamic GnRH clock in men, J. Clin. Endocrinol. Metab. 96(6):E908-15).

TABLE 1

| Plasma stability of Peptide 6 | |
|---|---|
| Incubation Time (minutes) | % Mean Compound Remaining |
| 0 | 100.0 |
| 30 | 118.9 |
| 60 | 93.7 |
| 90 | 97.2 |
| 120 | 71.8 |

Example 8

Effect of Peptide 6 on Spatial Learning and Memory in an Alzheimer Mouse Model 5XFAD Transgenic Mice 5XFAD mice overexpress the [APP K670N/M671L (Swedish)+I716V (Florida)+V717I (London) and PS1 M146L+L286V]. The generation of the 5XFAD mice has been described previously (Oakley, et al., 2006, J Neurosci 26(40):10129-40, 2006).

The effect of Peptide 6 on spatial learning and memory was tested in the Morris water maze behavioral test. At the acquisition phase, mice were given three to four trials per day on 6 consecutive days. In each trial, the mice were required to find a hidden platform located 1.5 cm below the water surface in a 1.1-m-diameter pool.

Within the testing room, only distal visual-spatial cues for location of the submerged platform were available. The escape latency, i.e., the time required by the mouse to find the platform and climb onto it, was recorded for up to 60 sec. Each mouse was allowed to remain on the platform for 20 sec and was then moved from the maze. If the mouse did not find the platform within 60 sec, it was manually placed on the platform for 20 sec. The interval between trials was 10 min. In the probe trial phase, the platform was removed from the pool and the location of each mouse in the pool was followed for 60 sec. Data were recorded using an EthoVision automated tracking system (Noldus).

For the reversal phase, mice were given four trials per day on 2 consecutive days, in this phase the platform was at a different location. Mice were either not treated (control), or treated with 8.75 µg/mouse of Peptide 6 by an intraperitoneal injection 30 minutes before testing. As seen from FIG. 6, mice treated with Peptide 6 (gray triangles) took less time than untreated mice (black squares) to find the platform on days 5 and 6 of the acquisition phase and days 1 and 2 of the reversal phase.

Overall the above result demonstrate that Peptide 6 is a potential drug candidate with higher efficiency and increased stability compared with Kp-10, wide therapeutic window and high tolerability.

REFERENCES

Alamed J., Wilcock D. M., Diamond D. M., Gordon M. N., Morgan D., Two-day radial-arm water maze learning and memory task; robust resolution of amyloid-related memory deficits in transgenic mice, *Nat. Protoc.* 2006, 1(4), 1671-1679.

Arai, A. C., and N. Orwig, Factors that regulate Kiss1 gene expression in the hippocampus, *Brain Res,* 2008, 1243, 10-18.

Arai A. C., The role of kisspeptin and GPR54 in the hippocampus, *Peptides* 2009, 30(1), 16-25.

Braff, D. L., and M. A. Geyer, Sensorimotor gating and schizophrenia. Human and animal model studies, *Arch Gen Psychiatry,* 1990, 47, 181-188.

Cardon, M., N. Ron-Harel, H. Cohen, G. M. Lewitus, and M. Schwartz, Dysregulation of kisspeptin and neurogenesis at adolescence link inborn immune deficits to the late onset of abnormal sensorimotor gating in congenital psychological disorders, *Mol Psychiatry,* 2010, 15, 415-425.

Castellanos, F. X., E. J. Fine, D. Kaysen, W. L. Marsh, J. L. Rapoport, and M. Hallett. Sensorimotor gating in boys with Tourette's syndrome and ADHD: preliminary results, *Biol Psychiatry* 1996, 39, 33-41.

Cryan J. F., Mombereau C., Vassout A., The tail suspension test as a model for assessing antidepressant activity: review of pharmacological and genetic studies in mice, *Neurosci Biobehav Rev,* 2005, 29, 571-625.

Ueki A., Goto K., Sato N., Iso H., and Morita Y., Prepulse inhibition of acoustic startle response in mild cognitive impairment and mild dementia of Alzheimer type. *Psychiatry Clin Neurosci.,* 2006, 60(1), 55-62.

Fridkin G., Rahimipour S., Ben-Aroya N., Kapitkovsky A., Di-Segni S., Rosenberg M., Kustanovich I., Koch Y., Gilon C., Fridkin M., Novel cyclic azo-bridged analogs of gonadotropin-releasing hormone, *J Pept Sci.,* 2006, 12(2), 106-115.

Fridkin G., Maina T., Nock B. A., Blat D., Lev-Goldman V., Scolnik Y., Kapitkovski A., Vachutinsky Y., Shechter Y. and Levy Y., Intramolecular azo-bridge as a cystine disulfide bond surrogate: Somatostatin-14 and brain natriuretic peptide (BNP) analogs, *Bioorg Med Chem,* 2011, 19(2), 798-806.

Ornitz, E. M., G. L. Hanna, and J. de Traversa. Prestimulation-induced startle modulation in attention-deficit hyperactivity disorder and nocturnal enuresis. *Psychophysiology,* 1992, 29, 437-451.

Ozawa, K., K. Hashimoto, T. Kishimoto, E. Shimizu, H. Ishikura, and M. Iyo, Immune activation during pregnancy in mice leads to dopaminergic hyperfunction and cognitive impairment in the offspring: a neurodevelopmental animal model of schizophrenia, *Biol Psychiatry,* 2006, 59, 546-554.

Perry, W., A. Minassian, B. Lopez, L. Maron, and A. Lincoln, Sensorimotor gating deficits in adults with autism, *Biol Psychiatry,* 2007, 61:482-486.

Steru L., Chermat R., Thierry B., Simon P., The tail suspension test: a new method for screening antidepressants in mice. Psychopharmacology (Berl), 1985, 85, 367-370.

Swerdlow, N. R., J. Paulsen, D. L. Braff, N. Butters, M. A. Geyer, and M. R. Swenson. Impaired prepulse inhibition of acoustic and tactile startle response in patients with Huntington's disease, *J Neurol Neurosurg Psychiatry,* 1995, 58, 192-200.

Swerdlow, N. R., C. H. Benbow, S. Zisook, M. A. Geyer, and D. L. Braff, A preliminary assessment of sensorimotor gating in patients with obsessive compulsive disorder. *Biol Psychiatry,* 1993, 33, 298-301.

Swerdlow N R, Geyer M A. (1998) Using an animal model of deficient sensorimotor gating to study the pathophysiology and new treatments of schizophrenia. Schizophr Bull 24(2): 285-301.

The invention claimed is:

1. A synthetic peptide selected from the group consisting of:

(i) a cyclic or linear peptide:

(SEQ ID NOs: 2 and 1)
R₁-Xaa₁-Gly-Xaa₂-Xaa₃-Xaa₄-Xaa₅-NHR₂ wherein:

Xaa₁ is selected from the group consisting of Phe, Ile, Leu, Val, Nle and analogs thereof;

Xaa₂ is selected from the group consisting of Leu, Ile, Val, Nle, Phe and analogs thereof;

Xaa₃ is selected from the group consisting of Arg, Lys, homo-Arg, homo-Lys, Orn and analogs of Arg;

Xaa₄ is selected from the group consisting of Trp and analogs thereof;

Xaa₅ is selected from the group consisting of Tyr, His, O-methyl-Tyr and 2-hydroxy-3-methyl-Phe;

R₁ is selected from the group consisting of para-aminophenylalanine (Pap), NH₂C₆H₄(CH₂)₁₋₃CO, Fmoc-Pap, FMS-Pap and C₅-C₂₀ acyl-Pap, wherein said C₅-C₂₀ acyl is derived from a saturated or unsaturated C₅-C₂₀ fatty acid linked to the α-amino group of Pap; and R₂ is H or (CH₂)₀₋₄CH₃, and (ii) pharmaceutically acceptable salts thereof.

2. The synthetic peptide of claim 1, wherein said analogs of Arg are selected from the group consisting of L-2-amino-3-guanidino propionic acid and N-ω,ω-dimethyl-L-arginine;

said analogs of Trp are selected from the group consisting of β-(3-benzothienyl)-L-Ala, 6-methyl Trp, 5-methoxy-Trp, 5-hydroxy-Trp, 5-fluoro-Trp, 7-azatryptophpan, 5-bromotryptophan and 5-methyltryptophan;

said analogs of Phe are selected from the group consisting of 2-fluorophenylalanine, 4-fluorophenylalanine, 4-bromophenylalanine, 2-chlorophenylalanine, L-homophenylalanine, 4-nitrophenylalanine and α-methylphenylalanine; and said analogs of Leu or Val are selected from the group consisting of t-butyl-L-alanine, L-cyclohexylglycine and L-cyclopentylglycine.

3. The synthetic peptide of claim 1, wherein the peptide is: a cyclic peptide:

(SEQ ID NO: 4)
Pap-Phe-Gly-Leu-Arg-Trp-Xaa₁-NHR₂ wherein:
Xaa₁ is Tyr or His; and
R₂ is H or (CH₂)₀₋₄CH₃.

4. The synthetic peptide of claim 1, wherein the pepside is:

(SEQ ID NO: 6)
Pap-Phe-Gly-Leu-Arg-Trp-Tyr-NH₂.

5. A pharmaceutical composition comprising the synthetic peptide of claim 1 or a pharmaceutically acceptable salt thereof and a pharmaceutically acceptable carrier.

6. The pharmaceutical composition of claim 5, formulated for oral administration.

7. A method for the treatment of a disease or disorder presenting behavioral abnormalities associated with impairment of sensory gating function, depression or cognitive impairment, wherein said disease or disorder is selected from the group consisting of schizophrenia, autistic disorder, Huntington's chorea, obsessive-compulsive disorder, attention deficit hyperactivity disorder (ADHD), Alzheimer's disease (AD), Tourette's syndrome depression and cognitive impairment, comprising administering to a patient in need thereof a pharmaceutically effective amount of a peptide of claim 1 or a pharmaceutically acceptable salt thereof.

8. The method of claim 7, wherein said disease or disorder is schizophrenia.

9. The method of claim 7, wherein said disease or disorder is Alzheimer's disease (AD).

10. The method of claim 7, wherein said peptide has a sequence as set forth in SEQ ID NO: 6.

11. The method of claim 7, wherein said disease or disorder is depression or a cognitive impairment.

12. The method of claim 11, wherein said depression and/or said cognitive impairment are associated with schizophrenia or with Alzheimer's disease.

13. A synthetic peptide, wherein the peptide is (SEQ ID NO: 6)

|Pap-Phe-Gly-Leu-Arg-Trp-Tyr-NH$_2$| or pharmaceutically acceptable salts thereof.

14. A pharmaceutical composition comprising the synthetic peptide of claim 13 or a pharmaceutically acceptable salt thereof and a pharmaceutically acceptable carrier.

15. The pharmaceutical composition of claim 14, formulated for oral administration.

16. A method for the treatment of a disease or disorder presenting behavioral abnormalities associated with impairment of sensory gating function, depression or cognitive impairment, wherein said disease or disorder is selected from the group consisting of schizophrenia, autistic disorder, Huntington's chorea, obsessive-compulsive disorder, attention deficit hyperactivity disorder (ADHD), Alzheimer's disease (AD), Tourette's syndrome, depression and cognitive impairment, comprising administering to a patient in need thereof a pharmaceutically effective amount of a peptide of claim 13 or a pharmaceutically acceptable salt thereof.

* * * * *